(12) United States Patent
Butt et al.

(10) Patent No.: US 11,666,214 B2
(45) Date of Patent: Jun. 6, 2023

(54) METHODS AND SYSTEMS FOR MEASURING INTRAOCULAR PRESSURE USING SOUNDWAVES

(71) Applicants: Khalifa University of Science and Technology, Abu Dhabi (AE); The University of Birmingham, Birmingham (GB)

(72) Inventors: Haider Butt, Abu Dhabi (AE); Khamis Essa, Birmingham (GB); Matt Soanes, Birmingham (GB); Nader Vahdati, Abu Dhabi (AE)

(73) Assignees: KHALIFA UNIVERSITY OF SCIENCE AND TECHNOLOGY, Abu Dhabi (UA); THE UNIVERSITY OF BIRMINGHAM, Birmingham (GB)

( * ) Notice: Subject to any disclaimer, the term of this patent is extended or adjusted under 35 U.S.C. 154(b) by 0 days.

(21) Appl. No.: 17/476,016

(22) Filed: Sep. 15, 2021

(65) Prior Publication Data

US 2023/0079501 A1  Mar. 16, 2023

(51) Int. Cl.
*A61B 3/16* (2006.01)
*A61B 5/00* (2006.01)

(52) U.S. Cl.
CPC .............. *A61B 3/16* (2013.01); *A61B 5/7275* (2013.01)

(58) Field of Classification Search
CPC ................................ A61B 3/16; A61B 5/7275
See application file for complete search history.

(56) References Cited

U.S. PATENT DOCUMENTS

| | | | | |
|---|---|---|---|---|
| 4,928,697 | A * | 5/1990 | Hsu | A61B 8/10 600/402 |
| 2016/0317025 | A1* | 11/2016 | Lee | A61B 3/0041 |
| 2017/0024771 | A1* | 1/2017 | Flitsch | G06Q 30/0269 |
| 2018/0193194 | A1* | 7/2018 | Haeggstrom | A61F 9/00781 |
| 2019/0380871 | A1* | 12/2019 | Gutierrez | G16H 20/10 |
| 2021/0038078 | A1* | 2/2021 | Rizzo | A61B 3/165 |
| 2021/0052221 | A1* | 2/2021 | Panneer Selvam | A61B 5/681 |

OTHER PUBLICATIONS

Simen Hellesund, "Measuring the speed of sound in air using a smartphone and a cardboard tube", 2019 Phys. Educ. 54 035015 (Year: 2019).*

Zhou, B , "An ultrasound vibro-elastography technique for assessing papilledema", Ultrasound Med Biol. 2019;45(8):2034-2039.

(Continued)

*Primary Examiner* — Patrick Fernandes
*Assistant Examiner* — Joseph A Tombers
(74) *Attorney, Agent, or Firm* — Billion & Armitage

(57) ABSTRACT

Methods and systems for measuring the intraocular pressure of an eye in a human. The methods include directing an acoustic incident wave at the surface of the eye to generate a reflected wave, measuring the coefficient of reflection of the incident and reflected waves, and determining the intraocular pressure of the eye from the coefficient of reflection. Also disclosed are methods of diagnosing glaucoma and/or intraocular hypertension.

21 Claims, 12 Drawing Sheets

(56) References Cited

OTHER PUBLICATIONS

"BrightFocus Foundation. How is Eye Pressure Measured?", BrightFocus Foundation, https://www.brightfocus.org/glaucoma/article/howeye-pressure measured#:~:text=Your%20ophthalmologist%20will%20instruct%20you,fixed%20area%20of%20the%20cornea. Accessed Sep. 2019.
"Comsol Application Gallery. Acoustic reflection analyser for a water-sediment interface", https://uk.comsol.com/model/acousticreflection-analyzer-for-a-water-sediment-interface-30881. Accessed Sep. 2019.
"Comsol. Acoustic Module User's Guide", Stockholm, Sweden: Comsol; 2018. https://doc.comsol.com/5.4/doc/com.comsol.help.aco/AcousticsModuleUsersGuide.pdf. Accessed Oct. 2019.
"Comsol. Theory for the plane, spherical, and cylindrical radiation boundary conditions", https://doc.comsol.com/5.5/docserver/#!/com.comsol.help.aco/aco_ug_pressure.05.130.html. Accessed Jan. 2020.
"Dictionary.com. Definition of hydrostatic pressure", https://www.dictionary.com/browse/hydrostatic-pressure. Accessed Jan. 2020.
"Essilor News. The eye air puff test—why you can't hide from it", https://www.essilorusa.com/newsroom/the-eye-air-puff-test-why-youcant-hide-from-it. Accessed Oct. 2019.
"MedicineNet. Medical definition of intraocular pressure.", https://www.medicinenet.com/script/main/art.asp?articlekey=4014. Accessed Sep. 2019.
"Nice Pathways. Icare rebound tonometer to measure intraocular pressure", https://www.nice.org.uk/advice/mib57. Accessed Oct. 2019.
"Pew Research Centre. Mobile Fact Sheet", https://www.pewinternet.org/fact-sheet/mobile/. Accessed Oct. 2019.
"Vismed.trbchemedica.co.uk. The precorneal tear film", https://vismed.trbchemedica.co.uk/business-professionals/understanding-thetear-film/the-precorneal-tear-film. Accessed Jan. 2020.
"Your Glaucoma Eye Examination: Part 1. Your Eye Pressure", Glaucoma NZ. 2008 vol. 5, Issue: 1.
Aloy, M , et al., "Estimation of the mechanical properties of the eye through the study of its vibrational modes", PLOS One. 2017;12(9):e0183892.
Berdahl, JP , et al., "Intracranial pressure and glaucoma", Curr Opin Ophthalmol. Mar. 2010;21(2):106-111. https://doi.org/10.1097/ICU.0b013e32833651d8.
Bouzidi, Y , "Incidence-angle-dependent acoustic reflections from liquid-saturated porous solids", Geophys J Int. 2012;191(3):1427-1440.
Bower, A , "Constitutive models: Relations between Stress and Strain", Appl Mech Solids. 2008;1(1):1-1. http://solidmechanics.org/text/Chapter3_2/Chapter3_2.htm.
Chowdhury, Roy U, et al., "Intracranial Pressure and Its Relationship to Glaucoma: Current Understanding and Future Directions", Med Hypothesis Discov Innov Ophthalmol 2015;4(3):71-80.
De Moraes, CGV , et al., "Modalities of tonometry and their accuracy with respect to corneal thickness and irregularities", J Optom. 2008;1(2):43-49.
De Siqueira, MF , et al., "Estimation of Permeability, Porosity and Rock Compressibility Properties using Digital Rock Analysis Technique for a Heavy Oil Unconsolidated Sandstone Offshore Brazil", Search and Discovery; 2018, Article #30587.
Dukhin, A , et al., "Characterization of Liquids, Nano- and Microparticulates, and Porous Bodies Using Ultrasound", vol. 24. Amsterdam: Elsevier; 2010:91-125.
Ewen King-Smith, P , et al., "The Thickness of the Human Precorneal Tear Film: Evidence from Reflection Spectra", Investig Ophthalmol Vis Sci. 2000;41:3348-3359.
Farhood, QK , "Comparative evaluation of intraocular pressure with an air-puff tonometer versus a Goldmann applanation tonometer", Clin Ophthalmol. 2013;7:23-27.
Ghabezloo, S , et al., "Evaluation of a permeability porosity relationship in a low permeability creeping material using a single transient test", Int J Rock Mech Min Sci. 2009;46(4):761-768.

Glover, P , "Formation evaluation MSc course notes", http://homepages.see.leeds.ac.uk/~earpwjg/PG_EN/CD%20Contents/Formation%20Evaluation%20English/Chapter%205.PDF. Accessed Dec. 2019.
Hanspeter, HE , et al., "Cerebrospinal fluid exchange in the optic nerve in normal-tension glaucoma", Br J Ophthalmol. 2012;96:544-548.
Iliev, ME , et al., "Comparison of rebound tonometry with Goldmann applanation tonometry and correlation with central corneal thickness", Br J Ophthalmol 2006;90(7):833-835.
Kharmyssov, C , et al., "Optic nerve head damage relation to intracranial pressure and corneal properties of eye in glaucoma risk assessment", Med Biol Eng Comput. 2019;57:1591-1603.
Kitamura, K , et al., "Effects of pressure on pore characteristics and permeability of porous rocks as estimated from seismic wave velocities in cores from TCDP Hole-A", Geophys J Int. 2010;182(3):1148-1160.
Lee, V , "Mechanisms and facilitation of corneal drug penetration", J Control Release. 1990;11(1-3):79-90.
Leonard, D , "Refractive Indices of the Collagen Fibrils and Extrafibrillar Material of the Corneal Stroma", Biophys J.1997;72(3):1382-1387.
Martin, F , et al., "Reservoir engineering.", Standard handbook of petroleum and natural gas engineering. vol. 2. Texas, TX: Gulf Professional Publishing; 1996:1-362.
Martola, E , "Central and peripheral", Arch Ophthalmol. 1968;79(1):28-30.
Mashige, K , "A review of corneal diameter, curvature and thickness values and influencing factors", African Vis Eye Health. 2013;72(4):185-194.
McCafferty, S , et al., "Goldmann applanation tonometry error relative to true intracameral intraocular pressure in vitro and in vivo", BMC Opthalmol. 2017;17(1):215.
McMonnies, CW , "Glaucoma history and risk factors", J Optom. 2016;2017:71-78.
Nakakura, S , et al., "Icare rebound tonometers: review of their characteristics and ease of use", Clin Ophthalmol. 2018;12:1245-1253.
Prausnitz, M , "Permeability of Cornea, Sclera, and Conjunctiva: A Literature Analysis for Drug Delivery to the Eye", J Pharm Sci. 1998;87(12):1479-1488.
Rufer, F , et al., "White-to-white corneal diameter", Cornea. 2005;24(3):259-261.
Schwan, L , et al., "Sound absorption and reflection from a resonant metasurface: Homogenisation model with experimental validation", Wave Motion. 2017;72:154-172.
Seddeq, HS , "Factors Influencing Acoustic Performance of Sound Absorptive Materials", Australian J Basic Appl Sci. 2009;3(4):4610-4617.
Semeraro, F. , et al., "Diabetic Retinopathy: Vascular and Inflammatory Disease", J Diabetes Res. 2015;2015:1-16.
Shah, S , "Accurate intraocular pressure measurement-the myth of modem ophthalmology?", Ophthalmology, ISSN: 0161-6420. 2000;107(10):1805-1807.
Shao, P , et al., "Effects of Corneal Hydration on Brillouin Microscopy In Vivo", Investig Opthalmol Visual Sci, 2018, vol. 59, Issue: 7, p. 3020.
Shih, P , et al., "Estimation of the Corneal Young's Modulus In Vivo Based on a Fluid-Filled Spherical-Shell Model with Scheimpflug Imaging", J Ophthalmol. 2017;2017:1-11.
Sit, AJ , et al., "In vivo noninvasive measurement of Young's modulus of elasticity in human eyes: a feasibility study", J Glaucoma. 2017;26(11):967-973.
Sutton, B , "Smartphone Tonometer Provides Reliable Preliminary IOP", https://www.healio.com/news/optometry/20200114/smartphone-tonometer-provides-reliable-preliminary-iop#.
Tham, Y-C , et al., "Global Prevalence of Glaucoma and Projections of Glaucoma Burden through 2040", Ophthalmology, ISSN: 1549-4713. 2014;121(11):2081-2090.
Wang, YX , et al., "Intraocular pressure and its normal range adjusted for ocular and systemic parameters", The Beijing Eye Study 2011. 2018;13(5).

(56) References Cited

OTHER PUBLICATIONS

Wang, YX, et al., "Intraocular pressure and its normal range adjusted for ocular and systemic parameters. The Beijing Eye Study 2011", PLOS One. 2018;13(5):e0196926. https://dx.doi.org/10.1371/journal.pone.0196926.

Wu, Y, et al., "Development and validation of a machine learning, smartphone-based tonometer", Br J Ophthalmol. 2020;104:1394-1398.

Zadok, D, et al., "Pneumotonometry versus Goldmann tonometry after laser in situ keratomileusis for myopia", J Cataract Refract Surg, ISSN: 0886-3350. 1999;25(10):1344-1348.

* cited by examiner

METHODS AND SYSTEMS FOR MEASURING INTRAOCULAR PRESSURE USING SOUNDWAVES

BACKGROUND

The eye is arguably one of the most cherished organs in the human body. Deterioration of vision leads to large socioeconomic losses worldwide and the continued state of health of the eye is of upmost importance to individuals. Many eye diseases have risk factors that are modifiable to avoid or minimize vision loss. One such example is maintaining stable blood sugars to avoid diabetic retinopathy.

Glaucoma is another eye disease for which there are several known risk factors, including age, race, intraocular pressure (IOP), and having a known family history of the disease. For glaucoma, the IOP is a modifiable risk factor, and its measurement and maintenance are paramount in stopping the irreversible vision loss that can occur with the disease. IOP is a vital measurement in the continued healthy state of the human eye and is defined as "the pressure created by the continued renewal of fluids within the eye". A healthy IOP value is generally between about 10 mmHg and about 20 mmHg, and this healthy IOP is important for maintaining the optimal refractive properties of the eye. Ocular hypertension is caused by an imbalance in the production and/or drainage of aqueous fluid in the eye. This imbalance is most common in older adults, with the risk of imbalance increasing as an individual gets older. In 2013, an estimated 64.3 million people worldwide had glaucoma.

The current, "gold standard" method for measuring IOP is applanation tonometry, which works on the Imbert-Fick law. The Imbert-Fick law states that the force required to flatten or applanate a sphere (W) is equal to the product of the pressure inside the sphere (P) and the area applanated (A):

$$W = P \times A \qquad \text{Equation I}$$

In practice, numbing drops followed by a non-toxic dye are applied to the patient's eyes. A small tip indents an area of the cornea and the required force for this is measured.

Although applanation tonometry is considered the "gold standard", it does have some drawbacks. For example, applanation tonometry measurements have been shown to be susceptible to error, with some studies showing a measurement error of as much as 5 mmHg. The cut-off level of IOP that differentiates "normal" from "abnormal" is commonly held to be 21 mmHg, which means that applanation tonometry may produce as much as a 23.89% error rate.

One potential source of error for applanation tonometry lies in patients that have a thin central corneal thickness (CCT). The cornea is the transparent layer forming the front of the eye and having a thin cornea is itself an independent risk factor for glaucoma. Thin corneas can occur from birth, but many common laser eye surgical procedures also lead to thin CCT. The only way to determine whether an applanation tonometry reading is accurate or artificially low is to do a full eye examination including a measurement of CCT.

In addition to being potentially unreliable, the instruments used to perform applanation measurements of IOP are typically quite expensive.

A need exists for improved methods for detecting risk factors for glaucoma.

SUMMARY

The present invention is directed towards methods and systems for measuring an intraocular pressure (IOP) of an eye in a human.

In some embodiments, the inventive methods include directing an acoustic incident wave at the surface of an eye to generate a reflected wave, measuring a coefficient of reflection of the acoustic incident wave and the reflected wave, and determining the intraocular pressure of the eye from the coefficient of reflection. The acoustic incident wave may be generated by an electronic device that is positioned on a major axis of the human eye or at a first angle from the major axis.

In some embodiments, the inventive systems include a mobile telephone configured to emit an acoustic incident wave at the surface of the eye to generate a reflected wave and a microphone configured to detect the reflected wave. In some embodiments, the mobile telephone is configured to measure the sound intensity level of the reflected wave after the reflected wave has been detected by the microphone. In some embodiments, the mobile telephone is configured to determine a coefficient of reflection of the acoustic incident wave and the reflected wave.

In some embodiments, the inventive systems include a first electronic device configured to emit an acoustic incident wave at the surface of the eye to generate a reflected wave, a microphone configured to detect the reflected wave, and a second electronic device configured to measure a sound intensity level of the reflected wave after the reflected wave has been detected by the microphone. In some embodiments, the first electronic device is a mobile telephone. In still further embodiments the second electronic device is an oscilloscope. In some embodiments, the first electronic device is positioned at a first angle from a major axis of the human eye and/or the microphone is positioned at a second angle from the major axis of the human eye. In some embodiments, the first electronic device and the microphone are both positioned coplanar with the eye and/or the major axis of the human eye. In still further embodiments, the first electronic device and the microphone are each placed a distance from the eye that is equal to or greater than at least one wavelength of the acoustic incident wave.

In some embodiments, the present invention includes methods and systems to determine whether an individual has an increased risk for glaucoma or ocular hypertension. The inventive methods include directing an acoustic incident wave at the surface of the eye to generate a reflected wave, measuring a coefficient of reflection of the acoustic incident wave and the reflected wave, and determining whether the individual has an increased risk or risk factor for glaucoma or ocular hypertension from the measured coefficient of reflection.

In some embodiments, the present invention includes methods and systems to monitor the change in the IOP of an eye of an individual over a course of time. The inventive methods include directing an acoustic incident wave at the surface of the eye to generate a reflected wave, measuring a coefficient of reflection of the acoustic incident wave and the reflected wave, and comparing the measured coefficient of reflection (or an IOP value determined from that measured coefficient of reflection) against one or more previously measurements from that individual to determine a change in the IOP of the individual over some time span (e.g., over the course of hours, days, weeks, months, or years).

In some embodiments, the present invention includes methods and systems to diagnose an individual as having glaucoma or ocular hypertension. The inventive methods include directing an acoustic incident wave at the surface of the eye to generate a reflected wave, measuring a coefficient of reflection of the acoustic incident wave and the reflected wave, and using the measured coefficient of reflection to determine whether the individual has glaucoma or ocular hypertension.

This summary is intended to provide an overview of subject matter of the present disclosure. It is not intended to provide an exclusive or exhaustive explanation of the invention. The detailed description is included to provide further information about the present patent application.

BRIEF DESCRIPTION OF THE DRAWINGS

In the drawings, which are not necessarily, drawn to scale, like numerals may describe similar components in different views. The drawings illustrate generally, by way of example, but not by way of limitation, various embodiments discussed herein.

DETAILED DESCRIPTION

The present disclosure is directed to methods and systems for determining the IOP, or changes in the IOP, of a human eye. The improved, mobile methods of the present invention involve a procedure of firing sound waves at the eye from a predefined incident angle and measuring the coefficient of reflection. In physics, a reflection coefficient is a parameter that describes how much of a wave is reflected by the impedance discontinuity in a transmission medium and is equal to the ratio of the amplitude of the reflected wave to the incident wave with each expressed as phasors.

The methods can be conducted using a smartphone, which is widely accessible with over half of American adults over the age of 65 already owning one. Furthermore, as the inventive methods do not applanate the surface of the eye, the inventive methods provide a more convenient and comfortable method for measuring and/or monitoring IOP. With all these factors taken into consideration, the present inventive method is far superior to prior art methods of measuring IOP.

In some embodiments, the present invention includes a method of measuring the intraocular pressure of an eye in a human.

Figure 1:
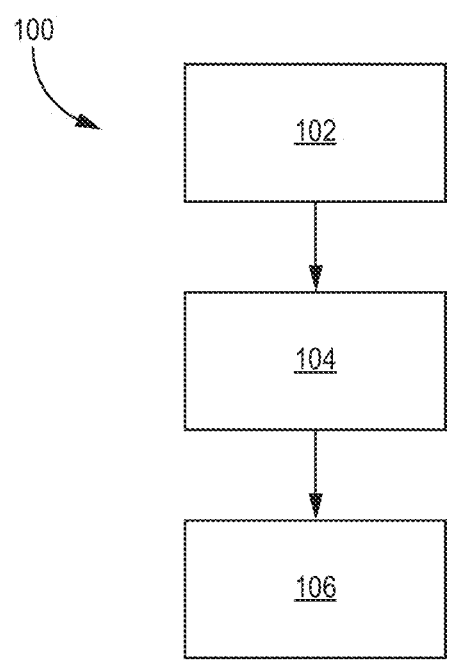
FIG. 1 is a graphical illustration of a process of the present invention.

FIG. 1 illustrates graphically process 100, which is just one example of a method of the present invention that is used to measure the IOP of a human eye. At part 102 of process 100, an acoustic incident wave is directed at the surface of the eye to generate a reflected wave. At part 104 of process 100, a coefficient of reflection of the acoustic incident wave and the reflected wave is measured. At part 106 of process 100, the IOP of the eye is determined from the measured coefficient of reflection.

Figure 2:
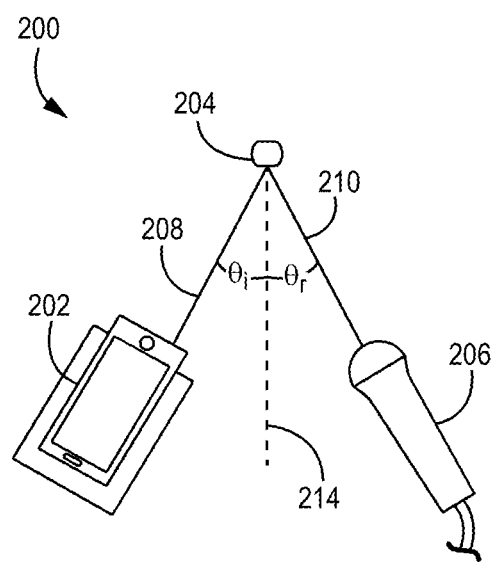
FIG. 2 illustrates articles and methods for directing an incident wave at the surface of an eye as part of the present invention.

FIG. 2 illustrates system 200 which provides articles and method for directing an incident wave at the surface of an eye. System 200 includes cell phone 202 and microphone 206, each positioned at an angle to major axis 214 of eye 204. Cell phone 202 emits acoustic incident wave 208 directed at eye 204. Incident wave 208 reflects off eye 204 to form or generate reflected wave 210. Microphone 206 detects reflected wave 210. Cell phone 202 is positioned relative to eye 204 such that incident wave 208 is emitted at angle $\theta_i$ relative to major axis 214 of eye 204. Reflected wave 210 is reflected from eye 204 at angle $\theta_r$ to major axis 214 of eye 204.

Cell phone 202 can be positioned relative to eye 204 such that angle $\theta_i$ of incident wave 208 to major axis 214 is equal to or between 0° and 90°. For example, cell phone 202 can be positioned such that angle $\theta_i$ is equal to or between 15° and 75°, is between 20° and 70°, is between 25° and 65°, is between 30° and 60°, is between 35° and 55°, or is between 40° and 50°. In further examples, cell phone 202 can be positioned such that angle $\theta_i$ is between 15° and 45°, is between 20° and 40°, or is between 25° and 35°. Cell phone 202 can be positioned such that angle $\theta_i$ is 0° (basically, directing incident wave 208 along major axis 214 of eye 204), 5°, 10°, 15°, 20°, 25°, 30°, 35°, 40°, 45°, 50°, 55°, 60°, 65°, 70°, 75°, 80°, 85°, 90°, or any incremental value or subrange between the angle values recited herein.

The angle $\theta_r$ of reflected wave 210 relative to major axis 214 is generally equal in magnitude to angle $\theta_i$, but opposite in direction. However, eye 204 may have a geometry or other aspects (e.g., a CCT or slight curvature of the eye's surface) that might cause the magnitude of angle $\theta_r$ to vary from the magnitude of angle $\theta_i$ by as much as ±20%, ±15%, ±10%, ±5%, or some incremental value or subrange therebetween. For example, if incident wave 208 has an angle that is 30° relative to major axis 214, then the resulting reflected wave 210 may have an angle $\theta_r$ that is −35° relative to major axis 214.

Cell phone 202 can be positioned such that angle $\theta_r$ of reflected wave 210 is between 0° and −90°. For example, cell phone 202 can be positioned such that angle $\theta_r$ is between −15° and −75°, is between −20° and −70°, is between −25° and −65°, is between −30° and −60°, is between −35° and −55°, or is between −40° and −50°. In further examples, cell phone 202 can be positioned such that angle $\theta_r$ is between −15° and −45°, is between −20° and −40°, or is between −25° and −35°. Cell phone 202 can be positioned such that angle $\theta_r$ is 0° (basically, directing reflected wave 210 along major axis 214 of eye 204), −5°, −10°, −15°, −20°, −25°, −30°, −35°, −40°, −45°, −50°, −55°, −60°, −65°, −70°, −75°, −80°, −85°, or −90°, or any incremental value or subrange between the angle values recited herein.

Cell phone 202 can emit an incident wave 208 with a frequency that results in the reflection coefficient having a positive correlation with the IOP of eye 204. As used herein, the term "driving frequency" refers to the frequency of the incident wave that is directed towards an eye. Suitable frequencies of incident wave 208 can be between 1,000 and 20,000 Hz. For example, the incident wave 208 frequency can be between 2,000 Hz and 19,000 Hz, between 3,000 Hz and 18,000 Hz, between 4,000 Hz and 17,000 Hz, between 5,000 Hz and 16,000 Hz, between 6,000 Hz and 15,000 Hz, between 7,000 Hz and 14,000 Hz, between 8,000 Hz and 13,000 Hz, between 9,000 Hz and 12,000 Hz, between 10,000 Hz and 11,000 Hz. For example, the incidence wave 208 frequency can be 1,000 Hz, 2,000 Hz, 3,000 Hz, 4,000 Hz, 5,000 Hz, 6,000 Hz, 7,000 Hz, 8,000 Hz, 9,000 Hz, 10,000 Hz, 11,000 Hz, 12,000 Hz, 13,000 Hz, 14,000 Hz, 15,000 Hz, 16,000 Hz, 17,000 Hz, 18,000 Hz, 19,000 Hz, 20,000 Hz, or any incremental value or subrange between the frequency values recited herein.

Figure 7A:
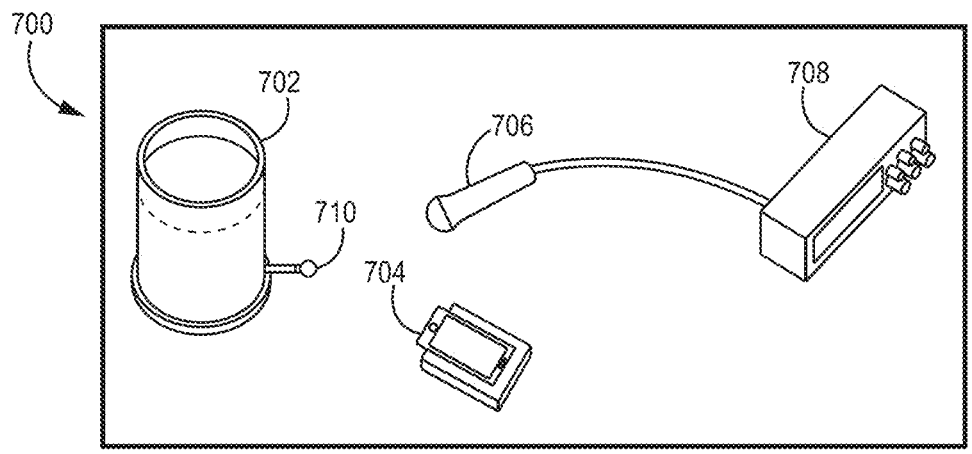
FIG. 7A-7C illustrates views of a system used to test methods of the present invention.
Figure 7B:
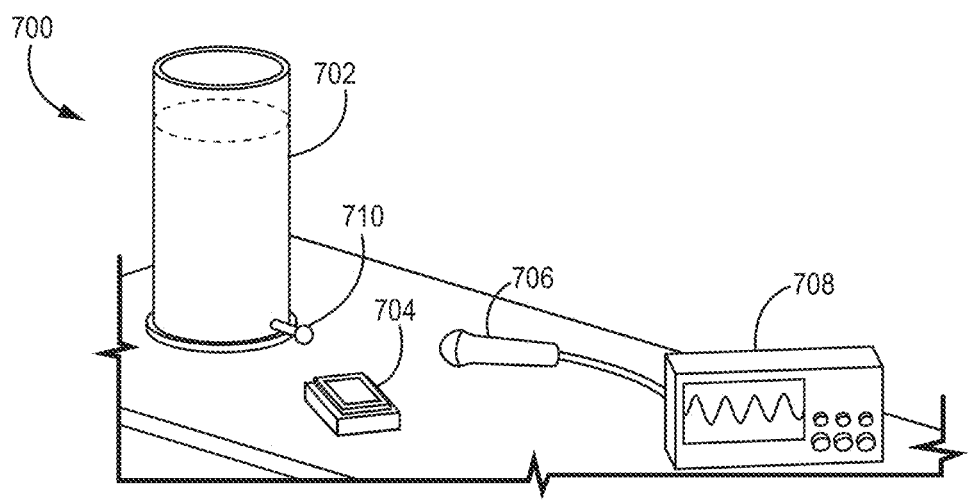

In some embodiments, cell phone 202 and microphone 206 are both positioned coplanar to major axis 214 of eye 204. For example, in FIG. 2, each of cell phone 202, microphone 206, and major axis 214 of eye 204 are all positioned in the plane of the paper (i.e., the plane represented by the page on which FIG. 2 is illustrated). FIGS. 7A and 7B, which are explained in more detail below, both illustrate cell phone 704 and microphone 706 both lying on the surface of a tabletop along with an artificial eye 710. While FIGS. 7A and 7B do not explicitly show the major axis of artificial eye 710, it is clear that all three of cell phone 704, microphone 706, and artificial eye 710 (and its major axis) are all roughly coplanar on the surface of the tabletop.

The distance that cell phone 202 and microphone 206 are positioned from eye 204 can be any distance that produces an acceptable measurement of the coefficient of reflection of the incident wave 208 and reflected wave 210. In some embodiments, one or both of those distances may be equal to some integer value of wavelengths of the incident wave 208 or reflected wave 210. For example, one or both of cell phone 202 and microphone 206 can be positioned a distance from eye 204 that is equal to 1, 2, 3, 4, 5, 6, 7, 8, 9, 10, 11, 12, 13, 14, 15, 16, 17, 18, 19, 20, or more than 20 wavelengths of incident wave 208 or reflected wave 210. In other embodiments, one or both of those distances may be equal to some fractional value of wavelengths of the incident wave 208 or reflected wave 210. For example, one or both of those distances may be equal to some fractional value of the wavelengths mentioned above.

While FIG. 2 illustrates cell phone 202, eye 204 and microphone 206 all lying within the same horizontal plane, in some embodiments the cell phone, eye, and microphone are all aligned in the same vertical plane. For example, cell phone 202 and microphone 206 could be positioned directly above or below axis 214 so that cell phone 202, microphone 206 and eye 204 are all coplanar in a plane that is normal to the plane of the paper and contains major axis 214.

Reflected wave 210 is detected by microphone 206. Microphone 206 is in electrical communication with an audio interface (not shown in FIG. 2) configured to measure the sound level of reflected wave 210. For example, the audio interface that is in communication with microphone 206 can be configured to measure the decibel level of reflected wave 210.

The coefficient of reflection of the acoustic incident wave 208 and reflected wave 210 can be measured by comparing the ratio of the sound level of incident wave 208 and reflected wave 210 using the following Equation II:

$$R_C = \left(\frac{A_R}{A_I}\right)^{-1} = \frac{A_I}{A_R} \quad \text{Equation II}$$

where $R_C$ is the reflection coefficient, $A_R$ is the average sound level of the reflected wave, and $A_I$ is the sound level of the incident wave.

The measured reflection coefficient is then used to determine the intraocular pressure of eye 204. For example, the reflection coefficient can be compared to cut-off values that provide an estimate of the intraocular pressure of eye 204 based upon predetermined reflection coefficient measurements. Alternatively, measurements of IOP and reflection coefficients from a population of human subjects can be used to produce a correlation function such that the measured reflection coefficient from a particular subject's eye can be inputted into the constructed correlation function to provide an estimate of the IOP of the particular subject's eye. In some embodiments, the correlation function also takes into account one or more of the subject's age, sex, race, and CCT. In some embodiments, the application asks the user for one or more of the subject's age, sex, race, or other medical history (e.g., whether the subject has undergone eye surgery) and uses the answers to those questions, along with the measured reflection coefficient, in determining the subject's IOP.

Further, the measured coefficient of reflection or IOP values from a particular individual can be compared to past measured coefficients of reflection or IOP values from that individual to determine whether the IOP of that individual has increased. For example, the measured coefficient of reflection or IOP values from a particular individual can be compared to measurements taken from that same individual over the previous 1, 2, 3, 6, 9, 12, 15, 18, 21, 24, 27, 30, 33, or 36 months on a daily, weekly, semi-monthly, or monthly basis. The compared measurements may be, for example, taken at approximately the same time of day (e.g., shortly after waking, after waking but before noon, after noon, or shortly before going to bed).

In some embodiments, the measured reflection coefficient is converted to an IOP measurement for the subject by an application running on a smartphone (e.g., the smartphone used to generate the incident wave and/or detect and measure the reflected wave).

While the acoustic incident wave may be generated by a cell phone (e.g., a smart phone), in some embodiments of the present invention the incident wave is generated by some other electronic device. For example, the acoustic incident wave may be generated by a speaker that is in electric communication with a laptop computer or a dedicated portable device designed to generate an audible signal with a predetermined frequency.

In some embodiments, the method of the present invention includes directing an acoustic wave generated by the electronic device (e.g., a cell phone) directly to the microphone to determine the incident wave amplitude. For example, the inventive methods could include a step of determining or confirming the incident wave amplitude by first directing an acoustic wave generated by the electronic device prior to directing an acoustic wave toward the eye of a subject.

In some embodiments, the methods of the present invention include placing a barrier between the electronic device that is generating the acoustic wave and the microphone that is detecting the reflected wave. For example, the method could include placing an acoustic barrier along part of the major axis of the eye of a tested subject to reduce or prevent the acoustic waves generated by the electronic device from travelling directly to the microphone used to detect a reflected wave. Alternatively, in some embodiments, a smartphone is used to both generate the acoustic incident wave and detect the reflected wave. For example, a speaker on a smartphone could be used to generate the incident wave and then a microphone on the smartphone could be used to detect the resulting reflected wave. The smartphone might use a time delayed measurement to differentiate the incident wave from the reflected wave. For example, the smartphone could be placed directly along the major axis of the eye such that the smartphone's speaker emits the incident wave directly along the major axis of the eye and the resulting reflected wave come back along the major axis and is detected by the smartphone's microphone.

In still further embodiments, the incident wave may be generated by the mobile phone and the microphone used to detect the resulting reflected wave is in electronic communication with the mobile telephone by, for example, a wire or via a wireless signal (e.g., a Bluetooth signal) to relay the detected reflected wave back to the mobile telephone. In this way, the mobile phone can be used to not only emit the incident wave but also measure the reflected wave that is detected by the microphone.

In some embodiments, the methods of the present invention are used to assess or detect a risk factor for glaucoma or ocular hypertension. For example, the methods for assessing a risk factor for glaucoma or ocular hypertension can include directing an acoustic incident wave at the surface of the eye to generate a reflected wave, measuring a coefficient of reflection of the acoustic incident wave and the reflected wave, determining the IOP of the eye, and assessing, detecting or determining the risk factor for glaucoma or ocular hypertension from the measured IOP. For example, the measured IOP can be compared to cut-off values that provide an estimate of whether the individual has a risk factor for glaucoma or ocular hypertension. Alternatively, the measured IOP can be compared to an average IOP measured in a population of healthy individuals and/or individuals that suffer from glaucoma and/or ocular hypertension, thereby providing an assessment of the tested individual's risk of glaucoma and/or ocular hypertension. Further, the measured IOP from a particular individual can be compared to past IOP measurements from that individual to determine whether the individual's IOP has increased and thereby detecting whether the individual's risk for glaucoma or ocular hypertension has increased since a previous measurement. For example, the measured IOP from a particular individual can be compared to measurements taken from that same individual over the previous 1, 2, 3, 6, 9, 12, 15, 18, 21, 24, 27, 30, 33, or 36 months on a daily, weekly, semi-monthly, or monthly basis. The compared measurements may be, for example, taken at approximately the same time of day (e.g., shortly after waking, after waking but before noon, after noon, or shortly before going to bed).

In some embodiments, the methods of the present invention are used to diagnose whether an individual has glaucoma or ocular hypertension. For example, the methods for diagnosing glaucoma or ocular hypertension in an individual can include directing an acoustic incident wave at the surface of the eye to generate a reflected wave, measuring a coefficient of reflection of the acoustic incident wave and the reflected wave, determining the IOP of the eye, and determining whether the individual has glaucoma or ocular hypertension from the measured IOP. For example, the measured IOP can be compared to cut-off values that provide an estimate of whether the individual has glaucoma or ocular hypertension. Alternatively, the measured IOP can be compared to IOP measurements in a population of healthy individuals and/or individuals that suffer from glaucoma and/or ocular hypertension, thereby providing an assessment of whether the tested individual has glaucoma or ocular hypertension. Further, the measured IOP from a particular individual can be compared to past IOP measurements from that individual to determine whether the individual has glaucoma or ocular hypertension. For example, the measured IOP from a particular individual can be compared to measurements taken from that same individual over the previous 1, 2, 3, 6, 9, 12, 15, 18, 21, 24, 27, 30, 33, or 36 months on a daily, weekly, semi-monthly, or monthly basis. The compared measurements may be, for example, taken at approximately the same time of day (e.g., shortly after waking, after waking but before noon, after noon, or shortly before going to bed).

In some embodiments, the methods of the present invention include placing ear plugs in the ears of the subject being tested prior to directing an acoustic wave at the individual's eye.

In some embodiments, the methods of the present invention include directing an individual to a medical professional for further examination or testing of intraocular pressure. The inventive methods and systems may also include monitoring an individual's coefficient of reflection or IOP over the course of a day, a week, a month, or some other time frame, and then providing those measured results to a medical professional for further review (e.g., for determining whether the patient has glaucoma or ocular hypertension or is at risk for such). By allowing self-monitoring, this invention can reduce the cost and inconvenience associated with a patient having to go to a hospital or clinic to get IOP measurements.

EXAMPLES

Example 1—Modeling

This experiment investigated whether the internal pressure of an eye-replicating object affects the reflection coefficient of acoustic waves. To test the validity of this approach, modeling software COMSOL Multiphysics (available from COMSOL, Inc. of Stockholm, Sweden) was utilized to prove a basic relationship between the reflection coefficient and IOP of the eye. COMSOL was used as it is a validated and trusted simulation software for reflection coefficient simulations.

Model construction: The model was constructed using a computational geometry to simulate an average human eye. Table 1 shows the geometry used for the simulation model and is based on an average between male and female values from literature.

TABLE 1

Simulation model geometry

| Parameter | Value (mm) |
| --- | --- |
| Diameter | 11.71 |
| Horizontal corneal curvature | 7.87 |
| Thickness of cornea | 0.55 |
| Thickness of precorneal tear film | 0.005 |

Figure 3A:
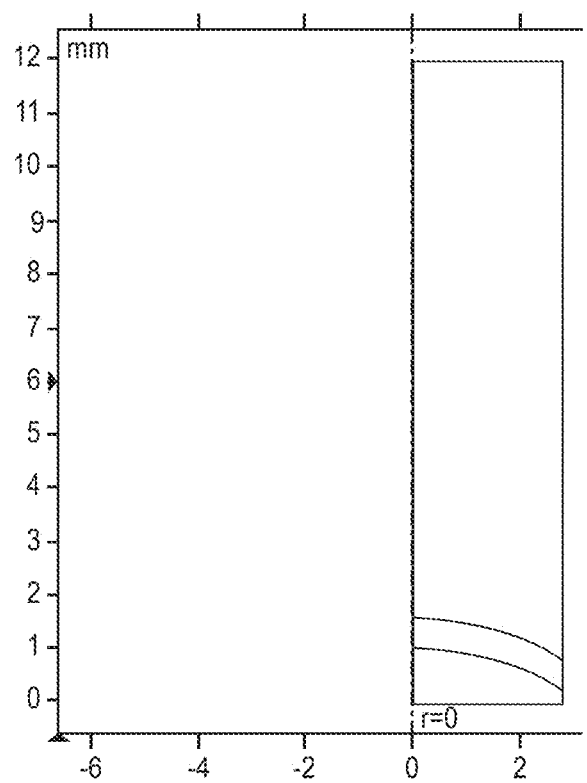
FIGS. 3A and 3B illustrate a 2D model of an average human eye constructed to conduct testing of reflection coefficients.
Figure 3B:
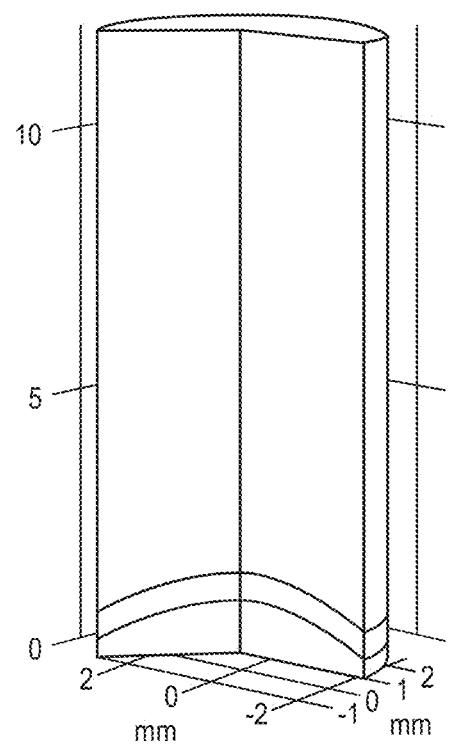

The 2D model is illustrated in FIG. 3(A). A 210° revolution image of the model is shown in FIG. 3(B). The model in FIG. 3(A) was constructed as a half-body model to exploit the 2D axisymmetric nature of the human eye and reduce computational time.

Knowledge of accurate precorneal tear film thickness is limited, with no consensus on the true value. Invasive methods have produced estimates in the range 4-10 μm, and this range is further supported by reflection spectra showing a peak at similar values. Thus, the value of 5 μm was estimated. Precorneal tear film structure consists of an inner mucus layer and an outer oily layer; however, the structure is dominated by the middle aqueous layer which is mostly water and dissolved nutrients. Therefore, for the simulation, the precorneal tear film layer was modeled as a water layer using the embedded software properties for water at room temperature.

As the geometry is curved, a perfectly matched layer could not be utilized to represent the open space. Thus, the boundaries were modeled as artificial boundary layers to simulate an open cavity as they do not represent physical walls.

The sound waves were assumed as high frequency (≥2,000 Hz) and highly localized due to the production of the sound wave from a local source. With these conditions, the sound source was modeled as a Gaussian pulse (a pulse with the temporal shape of a Gaussian distribution) of 1 mm radius. The use of a high frequency sound nullified the material thickness effect on absorption that affects low frequency incident sound waves. The incident pressure field was defined as cylindrical wave radiation as this allowed the pressure wave to leave the domain without spurious reflections based on the conditions of the simulation. During the simulation, the sound waves were reflected off the center of the cornea, thus a constant corneal thickness is assumed, although in reality, the thickness increases toward the periphery. In addition, it also assumed that there would be no reflection from the retina, isolating the reflections from the cornea.

Using the acoustics module within COMSOL Multiphysics, IOP could not be explicitly input as a parameter, thus, the relationship between IOP and a physical parameter that exploits the governing equations of the Pressure Acoustics, Frequency Domain was established.

Previous experiments for a wide range of applications have estimated the porosity of a material using its pressure, as in a lot of cases it is easier to measure pressure variations in changing conditions. As a result of this, many have formulated relationships estimating the porosity of a material using pressure, showing there is a relationship between the two parameters. Porosity is a parameter that can be explicitly used as a dependent variable in COMSOL Multiphysics, thus it can be used to prove an implicit relationship between pressure and reflection coefficient.

Porosity is a value between 0 and 1 that represents a fraction of the volume of pores in a material compared to total mass volume, usually ranging up to a maximum value of over 0.5 for peat or clay. For this reasoning, the porosity values were ranged from 0.1 to 0.6 to verify the relationship between porosity and reflection coefficient. Parameters input into COMSOL Multiphysics are outlined in Table 2:

TABLE 2

COMSOL Multiphysics input parameters

| Parameter | Value |
| --- | --- |
| Driving frequency sweep | 2,000-20,000 Hz in 1,000 Hz increments |
| Corneal porosity sweep | 0.1-0.6 in 0.1 increments |
| Density | 1,050 kg/m$^3$ |
| Permeability | 1.361 × 10$^{-11}$ |
| Youngs Modulus | 0.208 MPa |
| Poisson ratio | 0.49 |
| Bulk modulus | 3.47 × 10$^6$ Pa |
| Shear modulus | 6.98 × 10$^4$ Pa |

Figure 4:
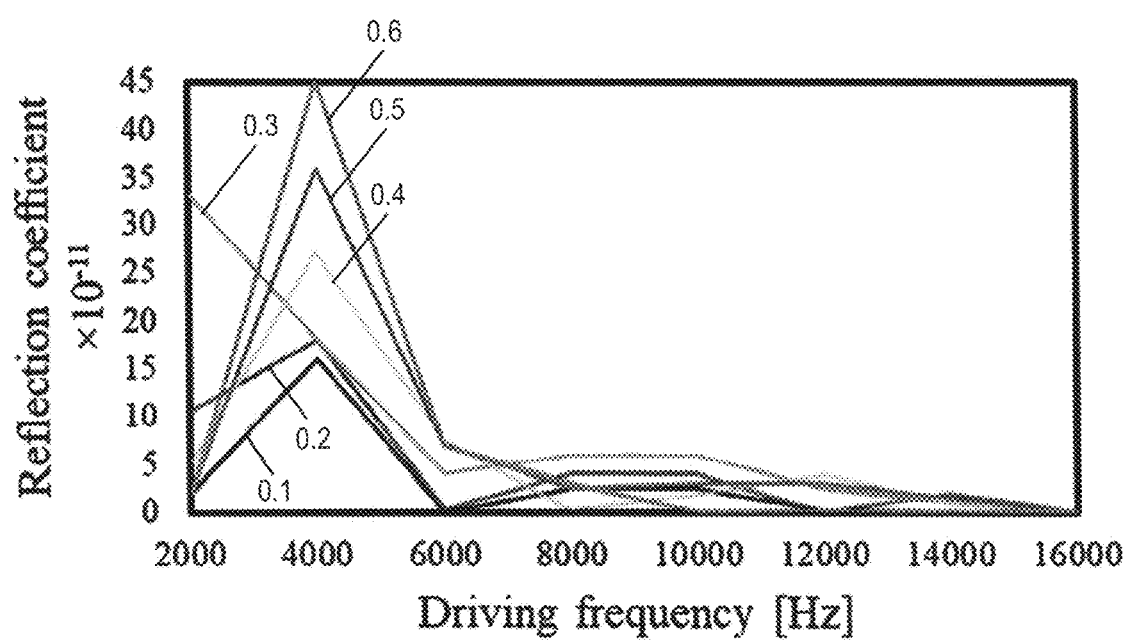
FIG. 4 illustrates a graph showing reflection coefficient measurements as a function of driving frequency.

Results: The geometry and parameter set up allowed an accurate model to be created and allowed a sweep of frequency and porosity. This was used to obtain results confirming the relationship between pressure and reflection coefficient. The results are shown in FIG. 4. FIG. 4 illustrates a graph of estimated reflection coefficients as a function of driving frequency for the modeled porosity values of 0.1, 0.2, 0.3, 0.4, 0.5, and 0.6. The graph shows that at lower frequencies (<6,000 Hz) the reflection coefficient shows a positive correlation with the material's porosity and thus the pressure. A porosity value of 0.2 showed an anomaly at a frequency of 2,000 Hz with a largely inflated value, likely due to inaccuracies of the modeling software at lower frequencies. As the frequency was increased in the range 6,000-20,000 Hz, the reflection coefficient converged to a reflection coefficient of 0, rendering these frequencies useless for experimentation. Due to the convergence to 0, FIG. 4 only shows the results up to 16,000 Hz. FIG. 4 shows that the most variation in reflection coefficients between porosity values is evident at a driving frequency of 4,000 Hz, and thus, we investigated this further.

Figure 5:
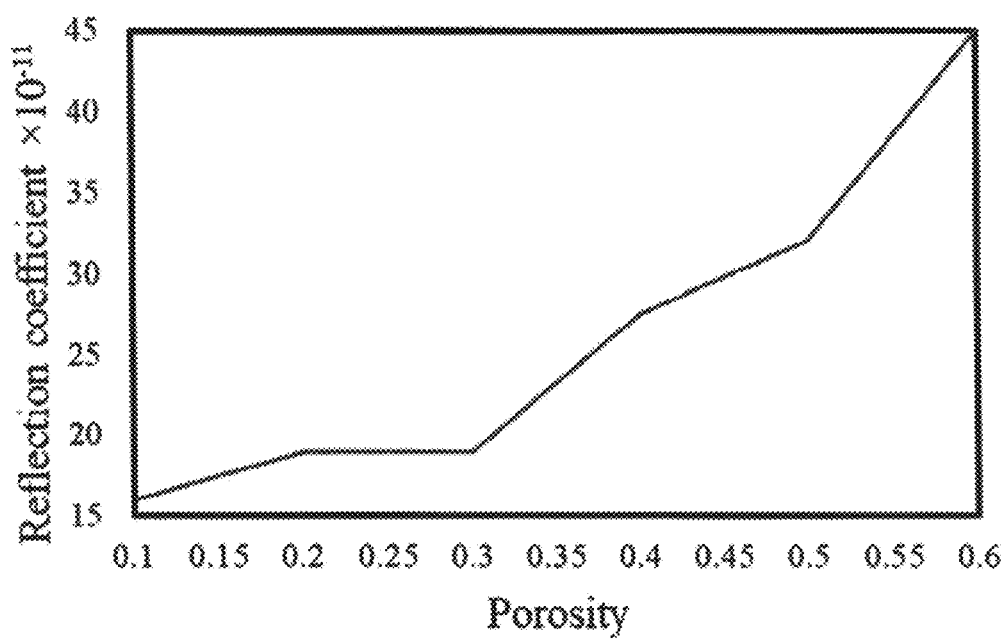
FIG. 5 illustrates a graph showing the relationship between porosity and reflection coefficient at a driving frequency of 4,000 Hz.

FIG. 5 shows another graph illustrating the relationship between porosity and reflection coefficient at a driving frequency of 4000 Hz. As can be seen, there was a significant positive correlation, thereby confirming the relationship between IOP and reflection coefficient and validating the worthiness of conducting further experiments.

Example 2—Physical Testing

Theory: To investigate the relationship between IOP and the reflection coefficient, an experiment was conducted. The experiment involved the application of the hydrostatic pressure theory to determine the pressure inside an object replicating the human eye. Hydrostatic pressure is defined as "the pressure exerted by a fluid at equilibrium at a given point within the fluid, due to the force of gravity. Hydrostatic pressure increases in proportion to depth measured from the surface because of the increasing weight of fluid exerting downward force from above." It follows the relationship shown by Equation III:

$$P = \rho g h \quad \quad \text{Equation III}$$

where
P is the pressure in the liquid at depth h (Pa);
ρ is the density of the fluid, which in these experiments is water with a density of 1,000 kg/m$^3$);
g is the gravitational constant 9.81 m/s$^2$; and
h is the depth of the fluid (m).

The 97.5% range of human eye pressure varies between 7.3 and 22.1 mmHg, equating to approximately 950-2950 Pa. Solving for h in Equation III, this is a variation in depth of approximately 0.10 to 0.30 meters, with the measurement at a water depth of 0.30 m represents the reading of an eye with ocular hypertension.

Sound waves fired at the eye will experience a portion of the wave that will aim to pass through the medium, whereas the remaining wave energy will reflect off the medium at an angle equal to or similar to the angle of the incident wave, as illustrated by FIG. 2. The reflection coefficient of the medium is defined as the ratio of the reflected wave amplitude or intensity to the incident wave amplitude or intensity.

The material properties for the eye replicating object in the experimental method dictate the resonant frequency of the object. At resonance, the absorption of the material is maximized and the reflection coefficient will become problematic to analyze. For these reasons, an initial frequency sweep was performed at a constant pressure to identify the resonant frequency of the object and ensure it is avoided in further experimentation.

The geometry of incident surfaces is exploited in acoustics in conjunction with material properties to significantly alter the reflection of sound waves in applications such as soundproofing rooms and optimizing sound quality in recording studios. By keeping the geometry of the replica eye constant throughout the experimentation will nullify the effect.

Figure 6:
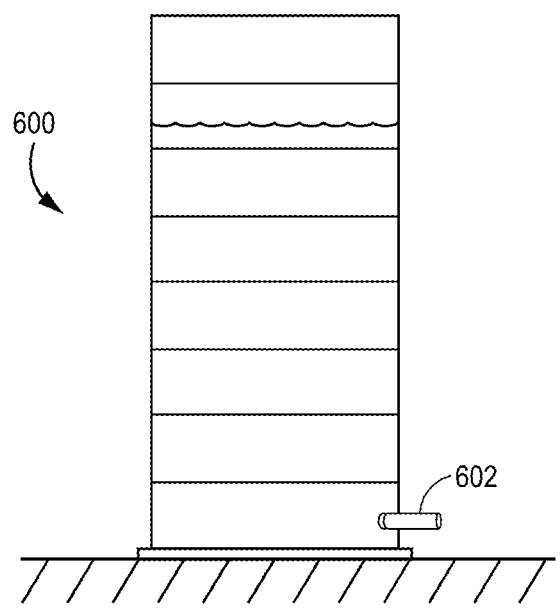
FIG. 6 illustrates a water tower used in the testing of methods of the present invention.

Experimental method: The depth of water was varied using a graduate water tower, as illustrated in FIG. 6 as water tower 600. Water tower 600 includes nozzle 602 near the base for the attachment of a replica eye.

A latex balloon secured to the end of a plastic tube was used as the replica eye, due to its benefit of retaining its geometry with varying levels of pressure. Sound waves were generated using a smartphone (iPhone 8; available from Apple, Inc. of Cupertino, Calif.) application "Tone generator" (made by Michael Heinz and available on the Apple, Inc. App Store). The lower right speaker of the smartphone was isolated for the experiment. A Zoom U-44 Handy Audio Interface (available from Zoom North America, of Hauppauge, N.Y.) and an sE SE1A microphone (obtained from sE Electronics International, Inc. of Shanghai, China) were used in conjunction with computer software Audacity (a popular open source digital audio editor and recording application software available at www.audacityteam.org) as an oscilloscope to analyze the sound waves.

Figure 7C:
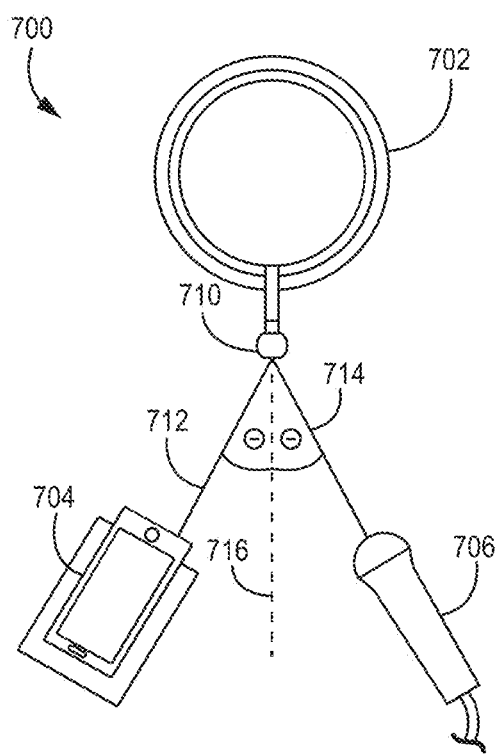

FIGS. 7A-7C illustrate various views of system 700 used in the experiment. System 700 includes water tower 702, smartphone 704, microphone 706, and audio interface 708. Water tower 702 includes artificial eye 710. As best shown in FIG. 7C, which is a top-down view of system 700, smartphone 704 was situated at angle θ to major axis 716 of eye 710. Incident wave 712 from smartphone 704 was directed at eye 710. Microphone 706 was situated at an angle that is equal and opposite to angle θ, thereby ensuring that reflected wave 714 was directed towards the center of microphone 706. Microphone 706 is in communication with audio interface 708. Audio interface 708 is electronic device that is used to analyze the sound waves (e.g., measuring the sound intensity level of the reflected wave). For example, audio interface 708 could be an oscilloscope.

Smartphone 704 was positioned so that its sound wave source was placed a distance of at least one wavelength from the reflection boundary, which is a distance of 0.172 m for the minimum frequency of 2,000 Hz using Equation IV:

$$\lambda = c/f \quad \text{Equation IV}$$

where λ is the wavelength (m), c is the speed of sound at sea level (344 m/s), and f is the frequency (Hz).

To conduct the experiment, the sound wave was exposed to the artificial eye 710 for approximately 2 seconds, which was ample time for Audacity to provide a stabilized sound pattern for analysis.

Figure 9:
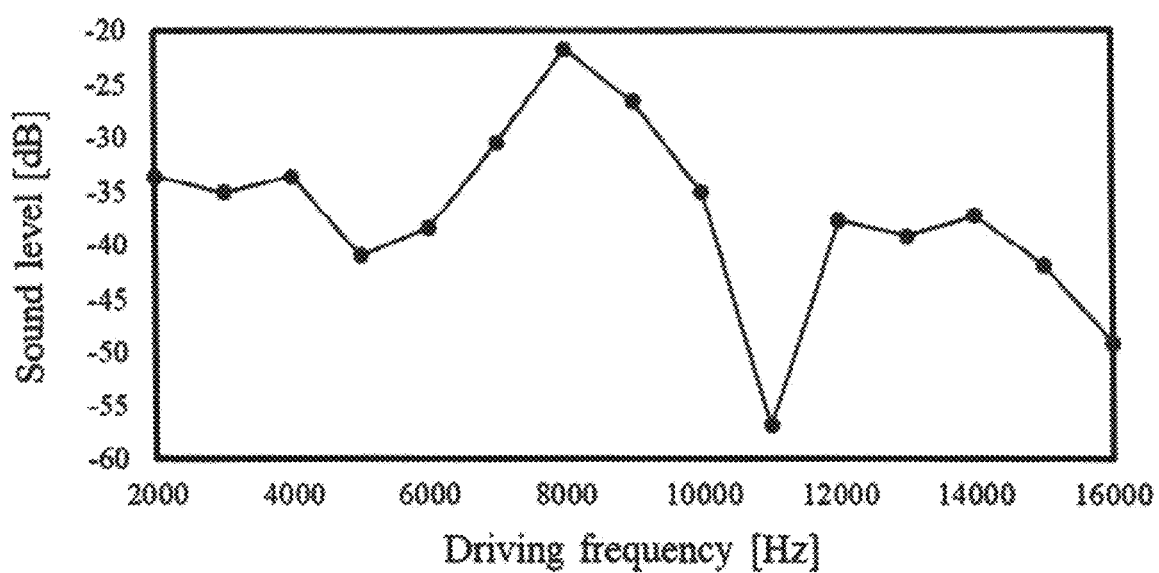
FIG. 9 illustrates a graph of sound levels detected at various driving frequencies.

The frequency sweep was conducted by increasing the frequency from 2,000 to 16,000 Hz in 1,000 Hz increments. The results of the peak amplitude at the driving frequencies are shown in Table 3 and illustrated in FIG. 9:

TABLE 3

Driving frequency versus peak sound level

| Driving frequency (Hz) | Sound level (dB) |
| --- | --- |
| 2,000 | −33.5 |
| 3,000 | −35.0 |
| 4,000 | −33.5 |
| 5,000 | −41.0 |
| 6,000 | −38.3 |
| 7,000 | −30.5 |
| 8,000 | −21.7 |
| 9,000 | −26.6 |
| 10,000 | −35.0 |
| 11,000 | −56.8 |
| 12,000 | −37.7 |
| 13,000 | −39.1 |
| 14,000 | −37.2 |
| 15,000 | −41.8 |
| 16,000 | −49.1 |

The frequency sweep was conducted using an incident wave angle θ of 30° and a water depth (h) of 0.175 m.

The internal pressure of the artificial eye was increased by increasing the water depth from 0.10 meters to 0.30 meters in 0.025-meter increments. The incident wave angle was again set at 30°.

The results are shown in Table 4:

TABLE 4

Depth of water versus reflection coefficients for driving frequency of 8,000 Hz

| Height of water (m) | Pressure (Pa) | Sound level, $1^{st}$ run (dB) | Sound level, 2 run (dB) | Sound level, $3^{rd}$ run (dB) | $A_R$ (dB) | $R_C$ |
| --- | --- | --- | --- | --- | --- | --- |
| 0.100 | 981 | −27.7 | −25.2 | −24.5 | −25.8 ± 1.7 | 0.65 |
| 0.125 | 1226 | −25.6 | −23.9 | −23.3 | −24.3 ± 1.2 | 0.68 |
| 0.150 | 1472 | −23.4 | −22.6 | −23.0 | −23.0 ± 0.4 | 0.72 |
| 0.175 | 1717 | −21.8 | −21.8 | −20.6 | −21.4 ± 0.7 | 0.78 |
| 0.200 | 1962 | −21.4 | −19.2 | −19.6 | −20.1 ± 1.2 | 0.83 |
| 0.225 | 2207 | −20.0 | −18.7 | −19.2 | −19.3 ± 0.7 | 0.86 |
| 0.250 | 2425 | −19.4 | −18.6 | −18.7 | −18.9 ± 0.4 | 0.88 |
| 0.275 | 2698 | −19.1 | −18.4 | −18.9 | −18.8 ± 0.4 | 0.88 |
| 0.300 | 2943 | −18.7 | −18.4 | −18.5 | −18.5 ± 0.2 | 0.90 |

Figure 8A:
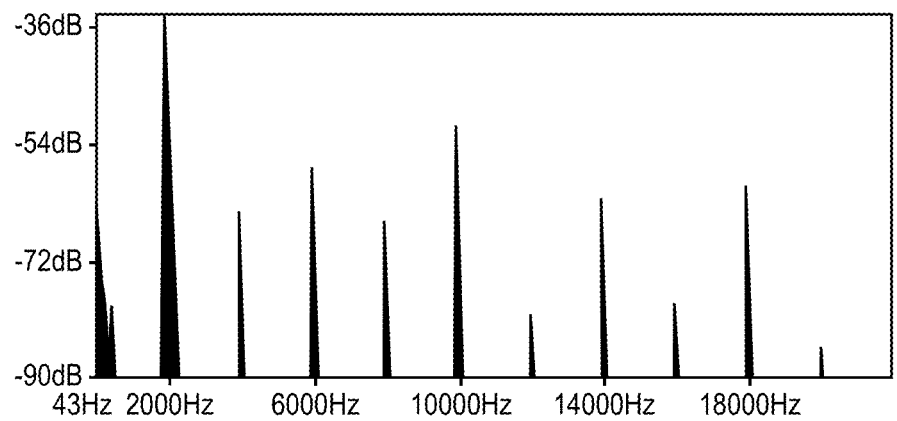
FIG. 8A illustrates a frequency spectrum produced on Audacity for a driving frequency of 2,000 Hz.
Figure 8B:
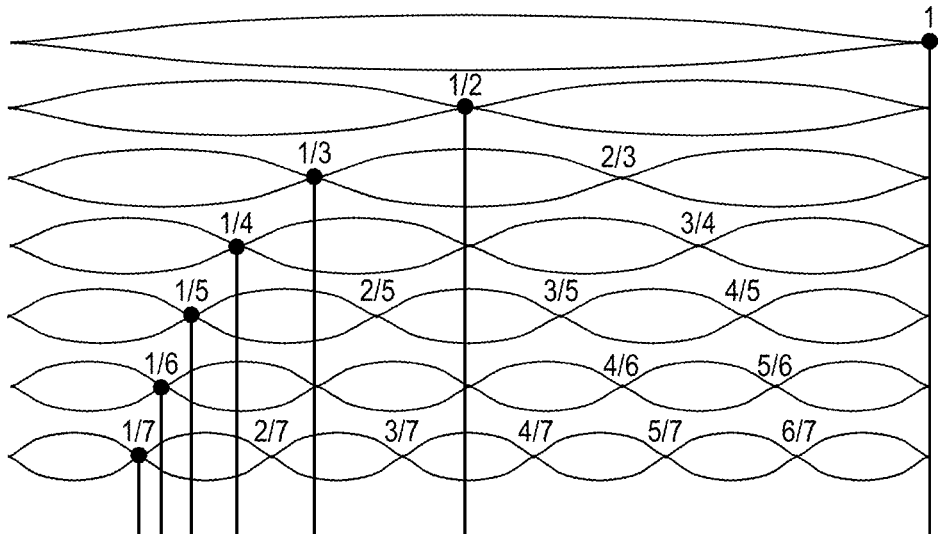
FIG. 8B illustrates a pictorial representation of the wave harmonics for the 2,000 Hz driving frequency.

FIG. 8A illustrates a frequency spectrum produced on Audacity for a driving frequency of 2,000 Hz. The subsequent peaks after the largest at 2,000 Hz were all at intervals of 2,000 due to the waves being harmonics of one another, as illustrated in FIG. 8B. This shows the first seven harmonics, which for the 2,000 Hz incident wave frequency, represent the peaks up to and including 14,000 Hz. This confirmed that FIG. 8A matched the theoretical frequency spectrum for an incident wave frequency of 2,000 Hz; and this trend continued for all frequency analysis conducted on Audacity. This also confirmed that there was negligible background noise interference in any of the sound recordings during the experiments. FIG. 8(A) also confirms the accuracy of the application ("Tone generator") used to generate the sound waves.

From these results it can be concluded that the resonant frequency for the replica eye was about 11,000 Hz and the optimal frequency for maximizing reflection was about 8,000 Hz. The results confirmed the theoretical pattern, where there was a frequency (11,000 Hz) which represented the resonant frequency of the material and absorption increased to a much higher value than at surrounding frequencies. There was also a frequency (8,000 Hz) where reflection was maximized, matching theoretical expectations. For at least these reasons, the results from the initial frequency sweep can be assumed as accurate.

With the optimal driving frequency determined, the incident wave amplitude was determined by firing an 8000 Hz sound wave directly at the microphone at the same distance as the reflected waves, resulting in a sound level of −16.6 dB. Supplementary results used to calculate an average are shown in Table 4. The standard deviation values provide an indication to the spread of the data, which were relatively low in this experiment. The standard deviations are increased by relatively higher values for all readings in the first completion of the experiment, shown in Table 4. However, all runs of the experiment showed the same relationship, so the elevation of the first run was considered as unimportant in the context of the experiment.

The reflection coefficients in Table 4 were calculated using Equation V:

$$R_C = \left(\frac{A_R}{A_I}\right)^{-1} = \frac{A_I}{A_R} \quad \text{Equation V}$$

where $R_C$ is the reflection coefficient, $A_R$ is the average sound level of the reflected wave (see Table 4), and $A_I$ is the sound level of the incident wave (which was −16.6 dB).

Note the sound level values in Audacity were negative. This was because the reference was a zero value, which represented the maximum sound level possible for analysis on Audacity before distortion. For this reason, Equation V was inverted, while its more common form is applicable to positive values of sound level. Some of the data illustrated in Table 4 is shown in FIG. 10, which illustrated the data for the reflection coefficient as a function of water depth.

The results showed that as the internal pressure of the artificial eye increased, the reflection coefficient also increased. Initially the increase showed a linear fashion, at a rate of approximately 1.80 $R_C$ per mmHg through the range 0.100-0.200 m. However, this rate decreased and begun to plateau as the pressure increased above a depth of 0.250 m. It can be concluded that there was a relationship between the internal pressure of the artificial eye and its acoustic reflection coefficient when other parameters were kept constant. These results also confirm that the present inventive methods could be used to monitor an individual's IOP and indicate when an individual was likely experiencing an increase in IOP so that such individuals could be subjected to closer monitoring of IOP and possibly examined for the prevalence or risk of glaucoma and/or ocular hypertension.

The reflection coefficients shown in Table 4 may be inflated as there was nothing preventing some soundwaves traveling directly from the source to the microphone without reflecting off the object. However, since the sound level of the source (the smartphone) and it's the positioning of the source and the microphone were invariable, it was assumed that the inflation would be the same for all readings of wave amplitude. Thus, it would not cause a misinterpretation of the relationship.

Figure 10:
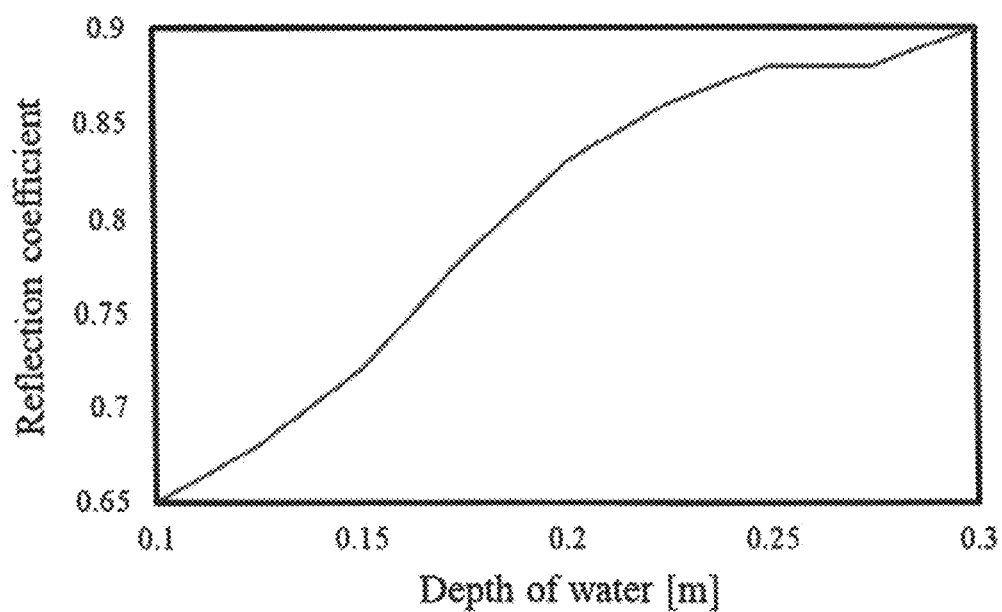
FIG. 10 illustrates a graph showing reflection coefficients as a function of water depth.

Following on from the results of this experiment, there appears to be a plateauing of the measured reflection coefficient as the pressure range moves into the area indicating hypertension in a patient's eye (approximately 0.25 m of water depth in FIG. 10). This could be due to the relatively larger values of reflection coefficient at a driving frequency of 8,000 Hz, shown in FIG. 9, a further experiment was conducted at a driving frequency of 6,000 Hz to investigate if the lower driving frequency would avoid or delay the observed plateauing effect.

Figure 11:
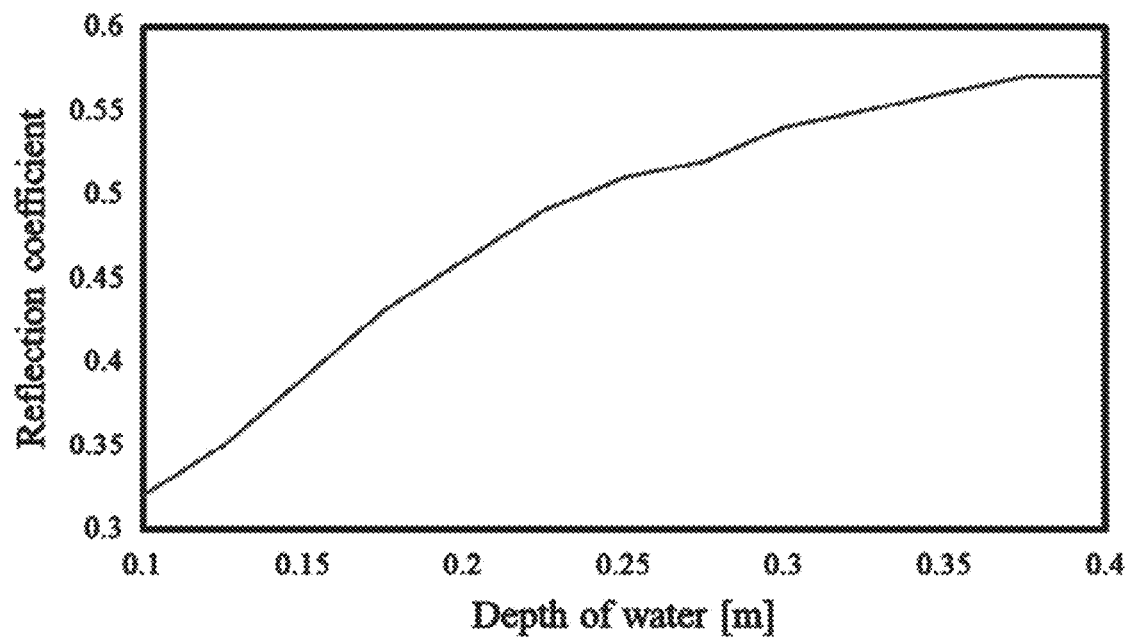
FIG. 11 illustrates a graph showing reflection coefficients as a function of water depth.

The experiment was conducted in an identical manner to the previous experiment, apart from the change of using a driving frequency of 6,000 Hz instead of 8,000 Hz and the depth of water range was increased to 0.10-0.40 meters to investigate the pressures beyond ocular hypertension. The baseline sound level recorded was −16.0 dB. The associated results are given in Tables 5 below and the reflection coefficient vs. the depth of water graph is provided in FIG. 11.

TABLE 5

Depth of water vs. reflection coefficient for a driving frequency of 6,000 Hz

| Height of Water (m) | Pressure (Pa) | Sound level, run 1 (dB) | Sound level, run 2 (dB) | Sound level run 4 (dB) | AR (db) | RC |
|---|---|---|---|---|---|---|
| 0.100 | 981 | −46.4 | −52.3 | −51.3 | −50.0 ± 2.6 | 0.32 |
| 0.125 | 1,226 | −42.6 | −48.0 | −46.4 | −45.7 ± 2.3 | 0.35 |
| 0.150 | 1,472 | −39.9 | −43.9 | −40.6 | −41.5 ± 1.7 | 0.39 |
| 0.175 | 1,717 | −36.0 | −39.2 | −36.5 | −37.2 ± 1.4 | 0.43 |
| 0.200 | 1,962 | −34.1 | −36.5 | −33.9 | −34.8 ± 1.2 | 0.46 |
| 0.225 | 2,207 | −32.1 | −34.5 | −32.0 | −32.9 ± 1.2 | 0.49 |
| 0.250 | 2,425 | −30.5 | −32.9 | −31.3 | −31.6 ± 1.0 | 0.51 |
| 0.275 | 2,698 | −28.7 | −32.8 | −30.9 | −30.8 ± 1.7 | 0.52 |
| 0.300 | 2,943 | −28.2 | −30.4 | −30.0 | −29.5 ± 1.0 | 0.54 |
| 0.325 | 3,188 | −28.8 | −29.8 | −28.8 | −29.1 ± 0.5 | 0.55 |
| 0.350 | 3,434 | −28.1 | −29.0 | −28.6 | −28.6 ± 0.4 | 0.56 |
| 0.375 | 3,679 | −27.8 | −28.4 | −28.2 | −28.1 ± 0.2 | 0.57 |
| 0.400 | 3,924 | −27.8 | −28.2 | −28.0 | −28.0 ± 0.2 | 0.57 |

As can be seen from these results, the same relationship was demonstrated with an increase in internal pressure of the artificial eye causing an increase in the reflection coefficient. The plateauing effect is delayed to values beyond those indicative of ocular hypertension, however the gradient of the relationship is smaller than the previous experiment.

Figure 12:
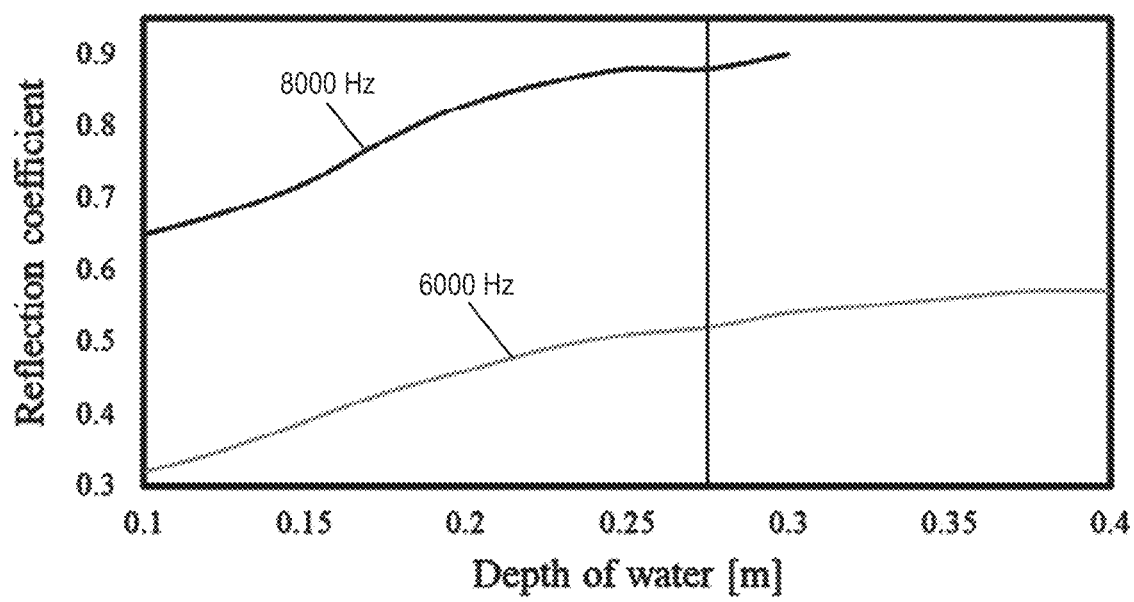
FIG. 12 illustrates a graph showing the reflection coefficient as a function of water depth for two different driving frequencies.

FIG. 12 shows a graph comparing the reflection coefficient of the sound waves for both incident wave frequencies of 6,000 and 8,000 Hz. The vertical line at 0.285 m represents the depth of water that indicates ocular hypertension. This value was calculated using Equation III and a pressure value of 22.1 mmHg (2,800 Pa). FIG. 12 clearly shows a delay in the plateauing of results past the hypertension indicative line for a 6,000 Hz driving frequency.

It should be noted that the soundwaves used in the experiments do produce audible sounds, some of which may cause discomfort to the patient. For this reason, the use of ear plugs may be desired.

In conclusion, a relationship was confirmed between internal pressure and acoustic reflection coefficient.

Thus, the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A method for measuring an intraocular pressure of an eye in a human, the method comprising:
    directing an acoustic incident wave at a surface of the eye, wherein ear plugs are placed in the ears of the human prior to directing the acoustic incident wave at the surface of the eye;
    reflecting the acoustic incident wave off an unapplanated surface of the eye to form an acoustic reflected wave, the acoustic reflected wave travelling away from the unappleanated surface of the eye;
    measuring a coefficient of reflection of the acoustic incident wave and the acoustic reflected wave, wherein measuring the coefficient of reflection includes measuring the sound intensity level of the acoustic reflected wave as the acoustic reflected wave travels away from the unapplanated surface of the eye and determining a ratio of a sound intensity level of the acoustic incident wave to the sound intensity level of the acoustic reflected wave; and
    determining the intraocular pressure of the eye from the coefficient of reflection.

2. The method of claim 1, wherein directing an acoustic incident wave at the surface of the human eye includes generating the acoustic incident wave from an electronic device that is positioned on a major axis of the human eye or at a first angle from the major axis.

3. The method of claim 2, wherein the electronic device is a mobile telephone.

4. The method of claim 2, wherein measuring the coefficient of reflection includes detecting the acoustic reflected wave with a microphone that is positioned on the major axis of the human eye or at a second angle from the major axis.

5. The method of claim 4, wherein the microphone is an in-built microphone in the mobile telephone or is in electronic communication with the mobile telephone.

6. The method of claim 5, wherein the mobile telephone is positioned on the major axis of the human eye.

7. The method of claim 5, wherein a time delayed based measurement is used to differentiate between the acoustic incident wave and the acoustic reflected wave.

8. The method of claim 1, further including placing a barrier between the electronic device and the microphone prior to directing an acoustic incident wave at the surface of the eye.

9. The method of claim 4, wherein the electronic device and the microphone are both coplanar with the major axis of the human eye.

10. The method of claim 9, wherein the first and second angles are equal in magnitude but opposite in degree.

11. The method of claim 4, wherein the electronic device and the microphone are each placed at a distance of at least one wavelength of the acoustic incident wave from the eye.

12. The method of claim 1, wherein the method is used to assess a risk factor for glaucoma or ocular hypertension.

13. The method of claim 12, further including directing the human to seek the services of a medical professional if the method indicates that there is an increased risk of glaucoma or ocular hypertension.

14. The method of claim 1, wherein the method is used to monitor the change in intraocular pressure of the eye over a period of at least 3 months.

15. The method of claim 14, wherein the method is performed daily at approximately the same time.

16. The method of claim 1, wherein the method is used to monitor the change in intraocular pressure of the eye over a period of at least 12 hours, wherein the method is performed multiple times during the 12 hour period.

17. The method of claim 1, wherein the method is used to diagnose that the human suffers from glaucoma.

18. The method of claim 1, wherein the acoustic incident wave has a frequency that maximizes the reflection of the acoustic wave from the eye.

19. The method of claim 1, wherein the acoustic incident wave has a frequency of between 2,000 Hz and 10,000 Hz.

20. The method of claim 19, wherein the acoustic incident wave has a frequency of between 6,000 Hz and 8,000 Hz.

21. The method of claim 1, wherein the acoustic incident wave is directed at the surface of the eye for a time period of 2 seconds or less.

* * * * *